(12) United States Patent
Pazenok et al.

(10) Patent No.: US 8,324,431 B2
(45) Date of Patent: Dec. 4, 2012

(54) PROCESS FOR PREPARING 2,4-DIHYDROXYPHENYL 4-METHOXYBENZYL KETONES

(75) Inventors: Sergii Pazenok, Solingen (DE); Norbert Lui, Odenthal (DE)

(73) Assignee: Plant Health Care, Inc., Pittsburgh, PA (US)

( * ) Notice: Subject to any disclaimer, the term of this patent is extended or adjusted under 35 U.S.C. 154(b) by 543 days.

(21) Appl. No.: 12/525,023

(22) PCT Filed: Feb. 16, 2008

(86) PCT No.: PCT/EP2008/001203
§ 371 (c)(1),
(2), (4) Date: Jul. 29, 2009

(87) PCT Pub. No.: WO2008/104297
PCT Pub. Date: Sep. 4, 2008

(65) Prior Publication Data
US 2010/0121082 A1    May 13, 2010

(30) Foreign Application Priority Data
Feb. 26, 2007  (EP) .................................. 07003860

(51) Int. Cl.
*C07C 49/00*   (2006.01)
*C07D 311/00*  (2006.01)
(52) U.S. Cl. ........................ 568/331; 549/403
(58) Field of Classification Search .................. 549/403; 568/338, 331
See application file for complete search history.

(56) References Cited

U.S. PATENT DOCUMENTS

| | | | |
|---|---|---|---|
| 4,225,619 A | 9/1980 | Brickl et al. | |
| 4,269,965 A | 5/1981 | Irwin | |
| 5,235,109 A | 8/1993 | Lanyi et al. | |
| 5,981,775 A | 11/1999 | Sreenivasan et al. | |
| 2006/0129002 A1 | 6/2006 | Wassmann-Wilken et al. | |

FOREIGN PATENT DOCUMENTS

| | | |
|---|---|---|
| EP | 0 295 883 A1 | 12/1988 |
| WO | 2005/054169 A1 | 6/2005 |

OTHER PUBLICATIONS

PCT/EP2008/001203 International Search Report, dated Jun. 2, 2008 (4 pages).
PCT/EP2008/001203 Written Opinion and English Translation, dated Jun. 2, 2008 (14 pages).
Colloidal Phenoxides. Part I. "The Relation Between Constitution and Colloidal Properties in Benzo-y-pyrones", Baker, W. and Eastwood, F.M., The Dyson Perrins Laboratory, Oxford, pp. 2897-2907, Oct. 21, 1929 (11 pages).
"Some Observations on the Use of Friedel & Crafts Reaction for the Synthesis of Desoxybenzoins", Gupta, S.R., Malik, K.K. and Seshadri, T.R., Indian J. Chem., vol. 6, Delhi, India, pp. 481-484, Sep. 1968 (4 pages).
"An Improved Procedure for the Acylation of Phenols Using Boron Trifluoride-Etherate", Mohanty, S. and Grover, S.K., Current Science, May 20, 1988, vol. 57, No. 10, pp. 537-538 (2 pages).
"Simple and Effective Synthesis of Isoflavones and 3-Aryloxychromones", Pivovarenko, V.G., Khilya, V.P. and Vasil'Ev, S.A., Chemistry of Natural Compounds, Sep.-Oct. 1989, vol. 25, No. 5, pp. 542-545 (5 pages).
"Microwave-promoted Synthesis of Polyhydroxydeoxybenzoins in Ionic Liquids", Hakala, U. and Wahala, K., Tetrahedron Letters 47, Oct. 6, 2006. pp. 8375-8378 (4 pages).

*Primary Examiner* — Taylor Victor Oh
(74) *Attorney, Agent, or Firm* — Buchanan Ingersoll & Rooney PC

(57) ABSTRACT

The invention relates to a process for preparing 2,4-dihydroxyphenyl 4-methoxybenzyl ketones of the formula (I) by Friedel-Crafts acylation in hydrogen fluoride (HF).

2,4-Dihydroxyphenyl 4-methoxybenzyl ketones of the formula (I) in which $R^1$ and $R^2$ are each hydrogen, chlorine, fluorine, bromine, iodine, $CF_3$, methyl, optionally substituted alkoxy, $-OCF_3$, $-C(CH_3)_3$, $-CH_2(CH_3)_2$, $-CH(CH_3)_2$, $R^3$ is hydrogen, Cl, F, Br, optionally substituted alkyl, optionally substituted alkoxy, $-C(CH_3)_3$, and X is hydroxyl, F, Cl, Br, optionally substituted alkoxy, are obtained in high yield and high purity by reacting phenylacetic acid derivatives of the formula (II) with phenols of the formula (III) in liquid hydrogen fluoride (HF).

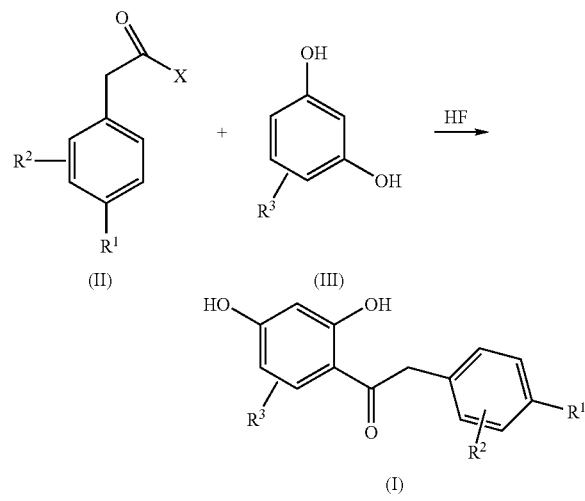

9 Claims, No Drawings

PROCESS FOR PREPARING 2,4-DIHYDROXYPHENYL 4-METHOXYBENZYL KETONES

The invention relates to a process for preparing 2,4-dihydroxyphenyl 4-methoxybenzyl ketones of the formula (I) by Friedel-Crafts acylation in hydrogen fluoride (HF).

2,4-Dihydroxyphenyl 4-methoxybenzyl ketones of the general formula (I) are important synthesis units for preparing isoflavones, for example for formononetin or genistein, daidzein and coumestrol (general formula (IV)).

2,4-Dihydroxyphenyl 4-methoxybenzyl ketones have, for example, been obtained with very moderate yield by the time-consuming Hoeben-Hoesch reaction proceeding from phenylacetonitrile, resorcinol and hydrogen chloride (W. Baker et al., J. Chem. Soc 1929, 2902).

The reaction of resorcinol and phenylacetic anhydride or of the free acid in the presence of boron trifluoride etherate with a yield of 67% has also been described (S. Mohaty et al., Current Science, May 20, 1988, vol. 57, N. 10 and U.S. Pat. No. 5,981,775).

In addition, a synthesis of deoxybenzoin from resorcinol and 4-methoxyphenylacetic acid in the presence of 40 molar equivalents of a $BF_3/Et_2O$ complex has been described (T. A. Hase in J. Chem Soc. Perkin Trans. 1, 1991, 3005).

Moreover, the synthesis of 2-phenylacetophenone derivatives from phenol and phenylacetic acid using dicyclohexylcarbodiimide (DCC) and 4-dimethylaminopyridine (DMAP) has been described (WO 2005/054169).

It is also known that benzoins can be obtained by means of Friedel-Crafts acylation in the presence of $AlCl_3$ (Indian J. Chem. vol. 6, 1968, p. 482).

Furthermore, it is known that polyhydroxybenzoins are obtainable by a microwave synthesis of ionic liquids in the presence of bis(trifluoromethyl)sulfonylamine or $BF_3/OEt_2$ (Tetrahedron Letters, 47, 2006, 8375).

All of these methods have a series of disadvantages. These are a low yield, long reaction times or the use of expensive reagents such as DCC and DMAP. The use of catalysts such as $BF_3$ and $AlCl_3$ generates large amounts of wastewater which has to be disposed of in a complicated manner.

The $BF_3/Et_2O$ complex is even unsuitable in practical terms for an industrial scale synthesis, since it possesses a very low flashpoint.

It has now been found that the synthesis of compounds (for example, 2,4-dihydroxyphenyl 4-methoxybenzyl ketones of the formula (I)

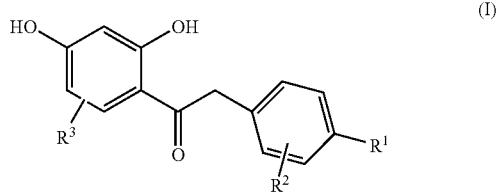

(I)

in which
$R^1$ and $R^2$ are each hydrogen, chlorine, fluorine, bromine, iodine, $CF_3$, methyl, methoxy, optionally substituted alkoxy, —$OCF_3$, —$C(CH_3)_3$, —$CH(CH_3)_2$,
$R^3$ is hydrogen, Cl, F, Br, or optionally substituted alkyl, optionally substituted alkoxy, —$C(CH_3)_3$, and
X is hydroxyl, F, Cl, or optionally substituted alkoxy or Br, is possible with high yield and in high purity by reacting phenylacetic acid derivatives of the formula (II) with phenols of the formula (III) in liquid hydrogen fluoride (HF).

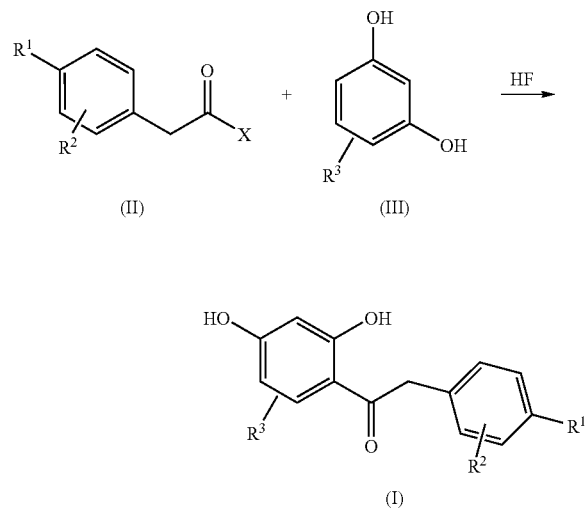

A further advantage of the process is that HF with a boiling point of 20° C. can be removed easily from the product by distillation and can therefore be recycled completely. HF is also a very inexpensive raw material and is prepared and used industrially on the thousand-tonne scale.

$R^1$ and $R^2$ are preferably hydrogen, methyl, methoxy, $C_1$-$C_6$-alkoxy, —$OCF_3$, —$C(CH_3)_3$,
—$CH(CH_3)_2$, or chlorine, fluorine, bromine, iodine, $CF_3$.

$R^1$ and $R^2$ are more preferably hydrogen, methyl, methoxy, $C_1$-$C_4$-alkoxy, —$C(CH_3)_3$,
—$CH(CH_3)_2$, or chlorine, fluorine, bromine, iodine, —$CF_3$.

$R^1$ is most preferably methoxy.

$R^2$ is most preferably hydrogen.

$R^3$ is preferably hydrogen, $C_1$-$C_6$-alkyl, chlorine, fluorine, bromine, $C_1$-$C_6$-alkoxy, —$C(CH_3)_3$.

$R^3$ is more preferably hydrogen, $C_1$-$C_4$-alkyl, Cl, F, Br, $C_1$-$C_4$-alkoxy, —$C(CH_3)_3$.

$R^3$ is most preferably hydrogen.

X is preferably hydroxyl, fluorine, chlorine, $C_1$-$C_6$-alkoxy, and more preferably hydroxyl, fluorine, chlorine, $C_1$-$C_4$-alkoxy.

X is also preferably bromine.

Possible substituents for alkyl and alkoxy are: fluorine, chlorine, bromine, iodine, $NO_2$, CN, SCN, NCO.

The reaction can optionally be accelerated by the addition of further catalysts. For example, catalysts, for example Lewis acids such as $BF_3$, $SbF_5$, $PF_5$, $BiF_3$, $AsF_3$, $AlCl_3$, $SbCl_5$, $TiCl_4$, $NbCl_5$, $SnCl_4$, $SiCl_4$ and $InCl_3$, may be used. Preferred catalysts are: $BF_3$, $SbCl_5$, $AlCl_3$, $SiCl_4$, $PF_5$. Particularly preferred catalysts are $BF_3$, $AlCl_3$, $SbCl_5$.

When performing the process according to the invention, the reaction temperatures can be varied within a relatively wide range. In general, the temperatures are between –10° C. and 120° C. The temperatures are preferably between 0° C. and 50° C. Particular preference is given to reaction temperatures between 20° C. and 40° C.

The molar ratios of the hydrogen fluoride to the phenol of the formula (III) are variable within a wide range. In general, the process according to the invention is performed with molar ratios of hydrogen fluoride to the phenol of the formula (III) between 1:1 and 100:1. Preference is given to molar ratios of 50:1 to 10:1.

The process according to the invention can optionally be performed in the presence of further diluents. Suitable such diluents are, for example, ether, Freon, dichloromethane, dichloroethane, toluene and chlorobenzene.

Preference is given to performing the process without further diluents.

The reaction can be performed at ambient pressure under autogenous pressure, or under the pressure of a protective gas.

The compounds of the general formula (I) can be converted to compounds of the general formula (IV) according to the following scheme.

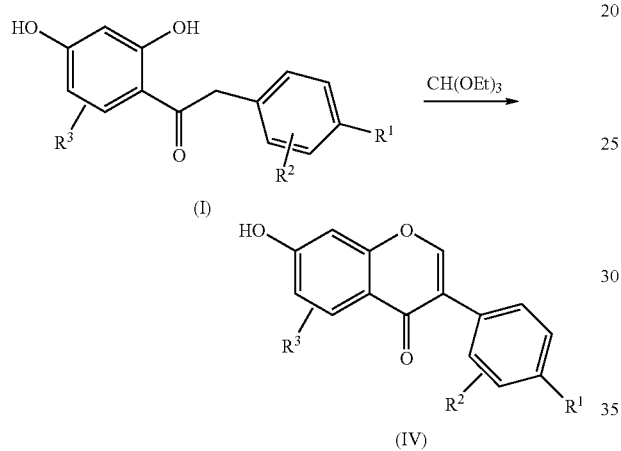

Suitable compounds for the reaction are, as well as $CH(OEt)_3$, general compounds which, as well as a CH structural unit, possess nucleophilic leaving groups (Pivovarenko et al., Klim. Pirod. Soed. (Ukraine) 5 (1989), 639-643).

PREPARATION EXAMPLES

Preparation of 1-(2,4-dihydroxyphenyl)-2-(4-methoxyphenyl)-ethanone

Example 1

4-Methoxyphenylacetic acid (83.9 g), resorcinol (55 g) and hydrogen fluoride (450 g) are initially charged in an autoclave at −10° C., and the mixture is stirred at 20° C. for 12 h. Subsequently, the hydrogen fluoride is evaporated off at 40° C., and the precipitate is washed with water and dried.

This affords 123 g (91% of theory) of the product with a purity of 96% and a melting point (m.p.) of 160-162° C.

Example 2

4-Methoxyphenylacetyl chloride (93 g), resorcinol (55 g) and hydrogen fluoride (450 g) are initially charged in an autoclave at −10° C., and the mixture is stirred at 20° C. for 12 h. Subsequently, the hydrogen fluoride is evaporated off at 40° C., and the precipitate is washed with water and dried.

This affords 125 g (92% of theory) of the product with a purity of 96%.

Example 3

4-Methoxyphenylacetic acid (83.9 g), resorcinol (55 g) and hydrogen fluoride (300 g) are initially charged in an autoclave at −10° C., and the mixture is stirred at 20° C. for 12 h. Subsequently, the hydrogen fluoride is evaporated off at 40° C., and the precipitate is washed with water and dried.

This affords 120 g (89% of theory) of the product with a purity of 93%.

The invention claimed is:
1. Process for preparing compounds of the formula (I)

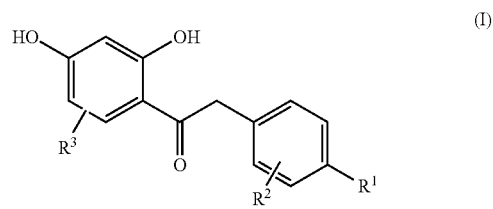

in which
$R^1$ and $R^2$ are each hydrogen, chlorine, fluorine, bromine, iodine, $CF_3$, methyl, alkoxy, —$OCF_3$, —$C(CH_3)_3$, —$CH(CH_3)_2$,
$R^3$ is hydrogen, Cl, F, Br, alkyl, alkoxy, —$C(CH_3)_3$, and
X is hydroxyl, F, Cl, Br, alkoxy,
by reacting compounds of the formula (II)

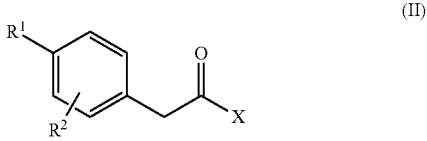

with phenols of the formula (III)

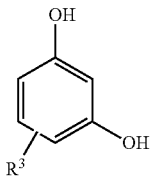

in hydrogen fluoride, wherein no further diluent is used.
2. Process according to claim 1, where
$R^1$ and $R^2$ are each hydrogen, chlorine, fluorine, bromine, iodine, $CF_3$, methyl, $C_1C_6$-alkoxy, —$OCF_3$, —$C(CH_3)_3$, —$CH(CH_3)_2$,
$R^3$ is hydrogen, Cl, F, Br, $C_1$-$C_6$-alkyl, $C_1$-$C_6$-alkoxy, —$C(CH_3)_3$, and
X is hydroxyl, F, Cl, Br, $C_1$-$C_6$-alkoxy.
3. Process according to claim 1, where
$R^1$ and $R^2$ are each hydrogen, chlorine, fluorine, bromine, iodine, $CF_3$, methyl, $C_1$-$C_4$-alkoxy, —$C(CH_3)_3$, —$CH(CH_3)_2$,
$R^3$ is hydrogen, Cl, F, Br, $C_1$-$C_6$-alkyl, $C_1$-$C_4$-alkoxy, —$C(CH_3)_3$, and
X is hydroxyl, F, Cl, $C_1$-$C_4$-alkoxy.
4. Process for preparing 1-(2,4-dihydroxyphenyl)-2-(4-methoxyphenyl)ethanone, characterized in that 4-methoxyphenylacetic acid or 4-methoxyphenylacetyl chloride is reacted with resorcinol and with hydrogen fluoride, without further diluents.

5. Process according to claim 1, characterized in that the molar ratio of hydrogen fluoride to the phenol of the formula (III) is in the range of 50:1 to 10:1.

6. Process according to claim 1, characterized in that the reaction temperature is between 10° C. and 50° C.

7. Process according to claim 1, characterized in that the reaction proceeds in the presence of a Lewis acid.

8. Process for preparing 1-(2,4-dihydroxyphenyl)-2-(4-methoxyphenyl)ethanone, characterized in that 4-methoxyphenylacetic acid or 4-methoxyphenylacetyl chloride is reacted with resorcinol and with hydrogen fluoride, without further diluents, at a molar ratio of hydrogen fluoride to resorcinol in the range of 50:1 to 10:1 and at a temperature in the range of 0° C. to 40° C.

9. Process for preparing compounds of the formula (IV)

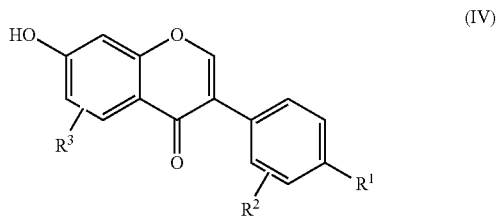

by reacting compounds of the formulae (II) with compounds of the formulae (III) according to claim 1 to form compounds of the formula (I) and then cyclizing the latter to flavones of the formula (IV).

* * * * *